US011317789B2

(12) United States Patent
Melsheimer

(10) Patent No.: US 11,317,789 B2
(45) Date of Patent: May 3, 2022

(54) ENDOSCOPE WITH CONTROL FOR TIP DEFLECTION

(71) Applicant: COOK MEDICAL TECHNOLOGIES LLC, Bloomington, IN (US)

(72) Inventor: Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 495 days.

(21) Appl. No.: 16/541,823

(22) Filed: Aug. 15, 2019

(65) Prior Publication Data

US 2020/0054194 A1 Feb. 20, 2020

Related U.S. Application Data

(60) Provisional application No. 62/765,041, filed on Aug. 17, 2018.

(51) Int. Cl.
*A61B 1/005* (2006.01)
*A61B 1/015* (2006.01)
*A61B 1/307* (2006.01)
*A61M 25/01* (2006.01)

(52) U.S. Cl.
CPC .......... *A61B 1/0052* (2013.01); *A61B 1/0057* (2013.01); *A61B 1/015* (2013.01); *A61B 1/307* (2013.01); *A61M 25/0136* (2013.01); *A61M 2025/015* (2013.01)

(58) Field of Classification Search
CPC ...... A61B 1/0052; A61B 1/0057; A61B 1/015
See application file for complete search history.

(56) References Cited

U.S. PATENT DOCUMENTS

| 4,559,928 | A  | * | 12/1985 | Takayama | A61B 1/0057 600/152 |
| 2008/0214896 | A1 | * | 9/2008 | Krupa | A61B 1/0052 600/141 |
| 2011/0208002 | A1 | * | 8/2011 | Kishioka | A61B 1/00052 600/146 |
| 2012/0071722 | A1 | * | 3/2012 | Nakamura | A61B 1/00078 600/140 |
| 2014/0012087 | A1 | * | 1/2014 | Omoto | A61B 1/051 600/146 |
| 2014/0088497 | A1 | * | 3/2014 | Campbell | A61B 1/0057 604/95.04 |
| 2014/0316202 | A1 | * | 10/2014 | Carroux | A61B 1/0052 600/146 |
| 2019/0350440 | A1 | * | 11/2019 | Leong | A61B 1/0052 |

* cited by examiner

*Primary Examiner* — Alexandra L Newton
*Assistant Examiner* — Rynae E Boler
(74) *Attorney, Agent, or Firm* — Crowell & Moring LLP

(57) ABSTRACT

A control for an endoscope includes a housing defining an interior volume. A lever external to the housing extends through the housing into the interior volume. A gear system positioned in the interior volume is operatively coupled to the lever. The gear system includes a first quadrant and a second quadrant each configured to pivot about a corresponding axis to deflect a flexible distal tip portion of the endoscope in a corresponding direction.

18 Claims, 6 Drawing Sheets

ENDOSCOPE WITH CONTROL FOR TIP DEFLECTION

CROSS-REFERENCE TO RELATED APPLICATIONS

This application is a non-provisional application which claims priority to U.S. provisional application Ser. No. 62/765,041, filed Aug. 17, 2018, which is incorporated by reference herein in its entirety.

BACKGROUND

Urological diseases affecting the urethra, bladder, ureters, and kidneys may be accessed, investigated, and treated with a minimally-invasive ureteroscope. Such a ureteroscope may include a "chip-in-tip" camera and lighting means, in addition to a suitable working channel and a deflectable or steerable tip. The working channel of a ureteroscope is configured to accommodate Lithotripsy devices, snares, lasers, and/or provide for the aspiration of stone fragments. The ureteroscope may also include a bilaterally deflectable tip that the operator can easily control so that the target site is reached and maintained in a timely manner. Further, reusable ureteroscopes may contribute to cross-contamination, may be worn and/or damaged during sterilization, and may require extra personnel, storage, and time.

SUMMARY

In an example embodiment, an endoscope includes a catheter having an elongate body with a proximal end and an opposing distal end. The elongate body includes at least one passage extending along a length of the elongate body between the proximal end and the distal end and a flexible distal tip portion coupled to the elongate body. A handle is coupled to the proximal end of the elongate body. The handle includes a housing defining an interior volume. A lever is positioned external to, e.g., on an outer surface of, the housing and extends through a thickness of the housing into the interior volume. A gear system positioned in the interior volume is operatively coupled to the lever. The gear system includes a first gear coupled to the lever. The first gear has a plurality of first teeth positioned about an annular surface of the first gear. The first gear is rotatable about a first axis as the lever is moved between a first position and a second position. A pinion is operatively coupled to the first gear. The pinion has an outer surface including a plurality of second teeth configured to cooperate with the plurality of first teeth such that the pinion rotates as the first gear rotates about the first axis. A worm gear is coaxially coupled to the pinion. The worm gear has at least one helical thread extending along a length of the worm gear. A gear nut is positioned about the worm gear. The gear nut cooperates with the at least one helical thread to move along the length of the worm gear as the worm gear rotates. The gear nut includes a first post and a second post extending laterally outward from the gear nut. A first quadrant contacts the first post such that as the gear nut moves in a first direction along a length of the worm gear the first post contacts the first quadrant to urge the first quadrant to pivot about a second axis. A second quadrant contacts the second post such that as the gear nut moves in a second direction opposite the first direction along a length of the worm gear the second post contacts the second quadrant to urge the second quadrant to pivot about a third axis collinear with the second axis. A first wire is coupled between the first quadrant and a first lateral side of the flexible distal tip portion and a second wire is coupled between the second quadrant and a second lateral side of the flexible distal tip portion opposite the first lateral side. Movement of the lever in a first direction urges the first quadrant to pivot about the second axis to provide tension in the first wire and deflect the flexible distal tip portion in a corresponding first direction and movement of the lever in a second direction different from the first direction urges the second quadrant to pivot about the third axis to provide tension in the second wire and deflect the flexible distal tip portion in a corresponding second direction.

In another example embodiment, a control for an endoscope system is provided. The endoscope system includes a catheter having a flexible distal tip portion. The control is coupled to a proximal end of the catheter and configured to control deflection of the flexible distal tip portion. The control includes a housing defining an interior volume. A lever is external to the housing and extends through the housing into the interior volume. A gear system positioned in the interior volume is operatively coupled to the lever. The gear system includes a first gear coupled to the lever. The first gear has a plurality of first teeth positioned about an annular surface of the first gear. The first gear is rotatable about a first axis as the lever is moved between a first position and a second position. A pinion is operatively coupled to the first gear. The pinion has an outer surface that includes a plurality of second teeth configured to cooperate with the plurality of first teeth such that the pinion rotates as the first gear rotates about the first axis. A worm gear is coaxially coupled to the pinion. The worm gear has at least one helical thread extending along a length of the worm gear. A gear nut is positioned about the worm gear. The gear nut cooperates with the at least one helical thread to move along the length of the worm gear as the worm gear rotates. The gear nut includes a first post and a second post extending laterally outward from the gear nut. A first quadrant contacts the first post such that as the gear nut moves in a first direction along a length of the worm gear the first post contacts the first quadrant to urge the first quadrant to pivot about a second axis. A second quadrant contacts the second post such that as the gear nut moves in a second direction opposite the first direction along the length of the worm gear the second post contacts the second quadrant to urge the second quadrant to pivot about a third axis collinear with the second axis, wherein movement of the lever in a first direction toward the first position deflects the flexible distal tip portion in a corresponding first direction.

In another example embodiment, a control for an endoscope system is provided. The endoscope system includes a catheter having a flexible distal tip portion. The control is coupled to a proximal end of a catheter and configured to control deflection of the flexible distal tip portion. The control includes a housing defining an interior volume. A lever external to the housing extends through the housing into the interior volume. A gear system is positioned in the interior volume and is operatively coupled to the lever. The gear system includes a worm gear operatively coupled to the lever. The worm gear having at least one helical thread extending along a length of the worm gear. A gear nut is positioned about the worm gear. The gear nut cooperates with the at least one helical thread to move along the length of the worm gear as the worm gear rotates. The gear nut includes a first cam and a second cam. A first quadrant has a first surface that contacts the first cam such that as the gear nut moves in a first direction along a length of the worm gear the first cam contacts the first surface to urge the first quadrant to pivot about a first axis. A second quadrant has a second surface contacting the second cam such that as the gear nut moves in a second direction opposite the first direction along a length of the worm gear the second cam contacts the second surface to urge the second quadrant to pivot about a second axis collinear with the first axis, wherein movement of the lever in a first direction urges the first quadrant to pivot about the first axis and deflect the flexible distal tip portion in a corresponding first direction and movement of the lever in a second direction different from the first direction urges the second quadrant to pivot about the second axis and deflect the flexible distal tip portion in a corresponding second direction.

BRIEF DESCRIPTION OF THE DRAWINGS

The detailed description is set forth with reference to the accompanying figures. The use of the same reference numbers in different figures indicates similar or identical items or features.

DETAILED DESCRIPTION

Example embodiments of the present invention are disclosed herein. It is understood, however, that the disclosed embodiments are merely exemplary and may be embodied in various and alternative forms. The figures are not necessarily to scale; some figures may be configured to show the details of a particular component. Therefore, specific structural and functional details disclosed herein are not to be interpreted as limiting but merely as a representative basis for the claims and/or teaching one skilled in the art to practice the embodiments.

Example embodiments seek to overcome some of the concerns associated with visualization of body pathways and cavities, which may be tortuous, during endoscopic and laparoscopic surgery. Example embodiments described a system including an access sheath, a dilator disposed at a distal end of the access sheath, and an imaging mini-scope removably coupled to the access sheath or dilator that may be used for endoscopic or laparoscopic surgical procedures including at least urological procedures, although the size and scale of the embodiments may be adapted for other procedures within the scope of the present disclosure.

Figure 3:
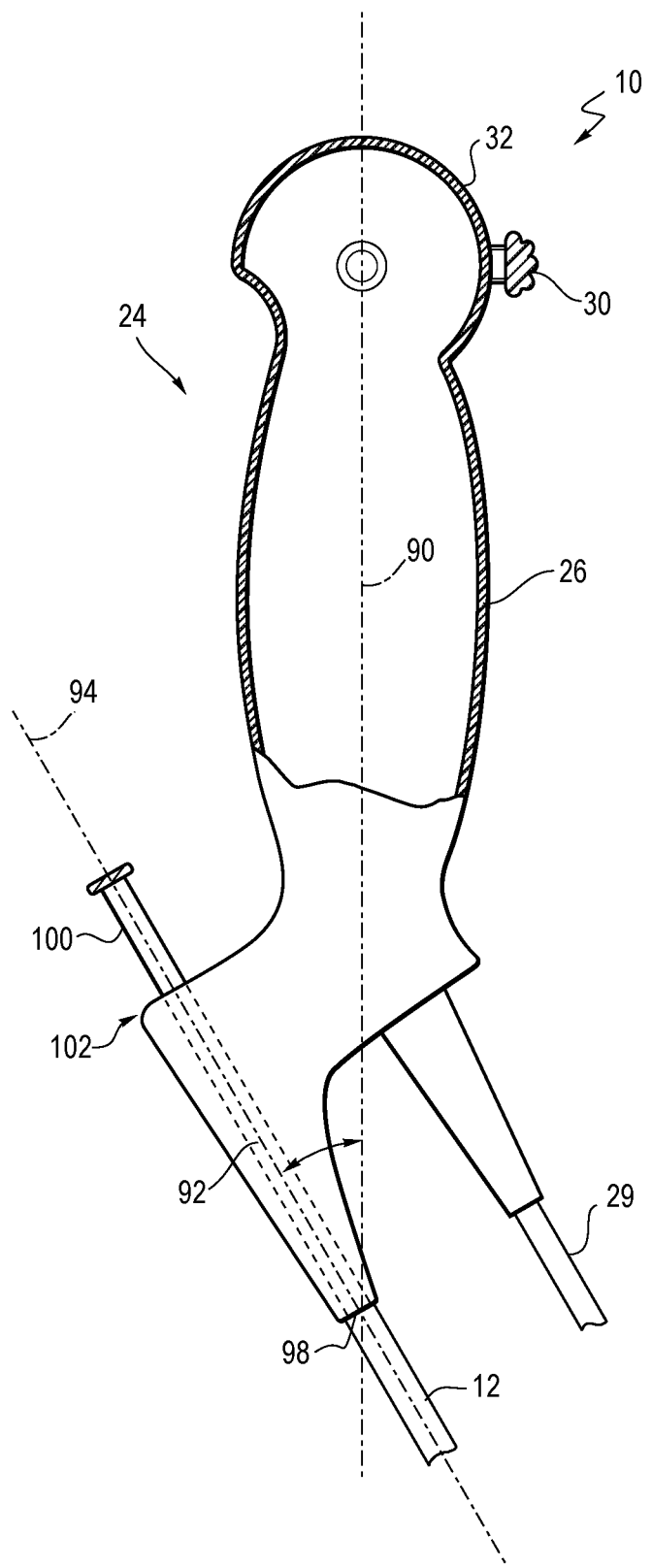
FIG. 3 is a plan view of an alternative example handle for an endoscope system, according to various embodiments.
Figure 4:
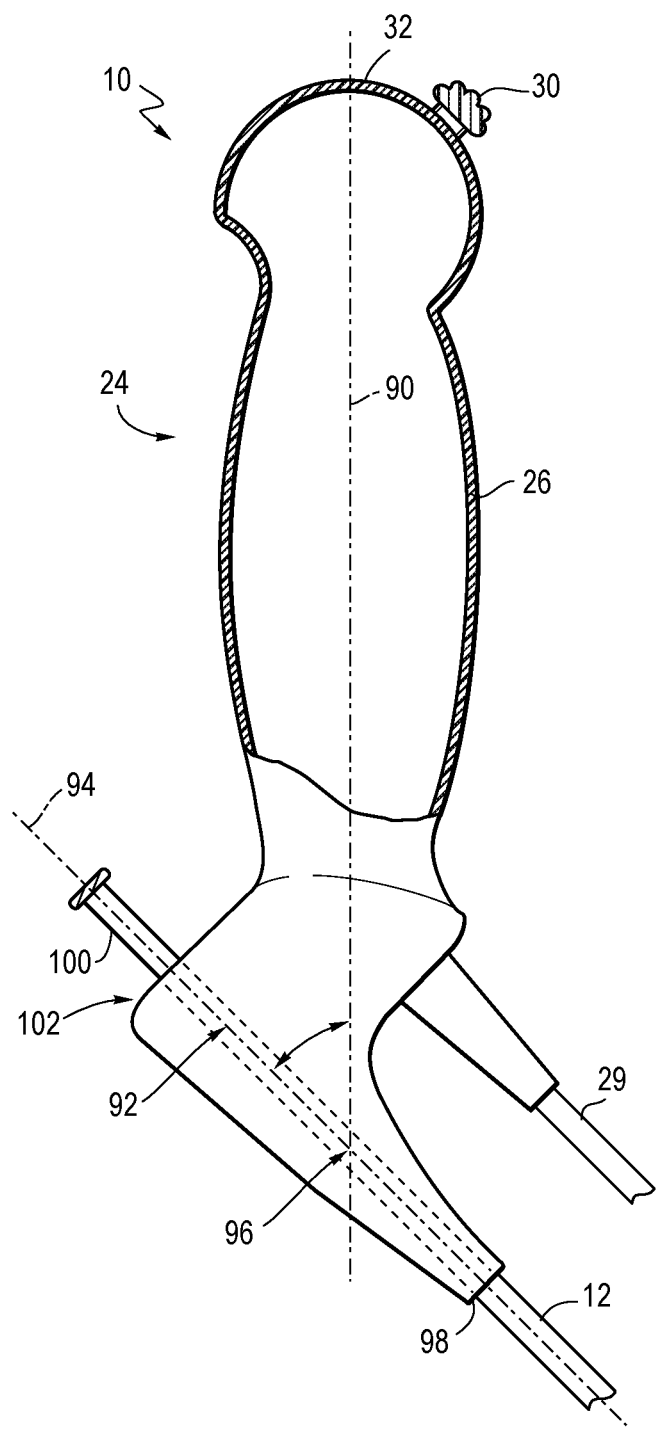
FIG. 4 is a plan view of an alternative example handle for an endoscope system, according to various embodiments.
Figure 5:
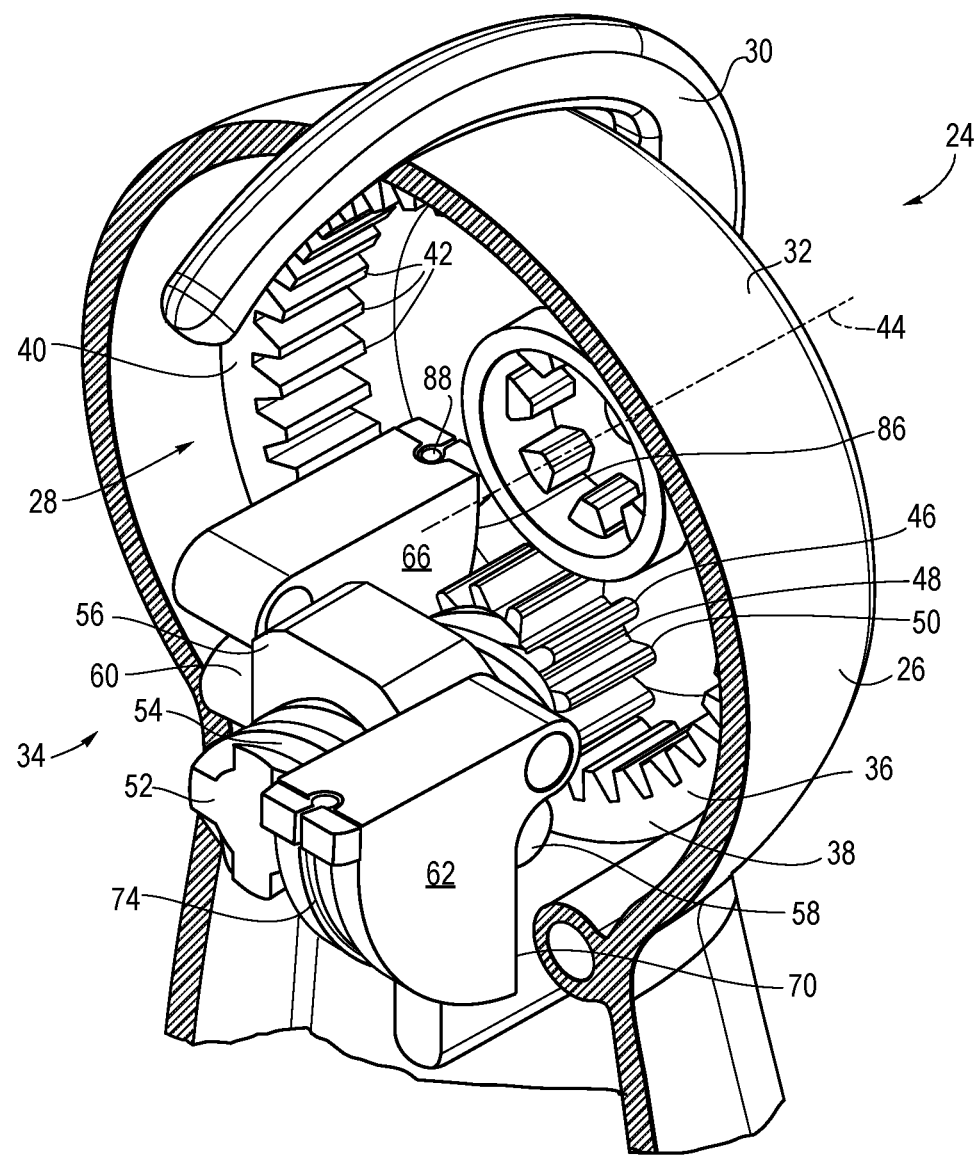
FIG. 5 is a sectional view of a portion of an example handle for an endoscope with a lever in an initial or neutral position, according to various embodiments.
Figure 6:
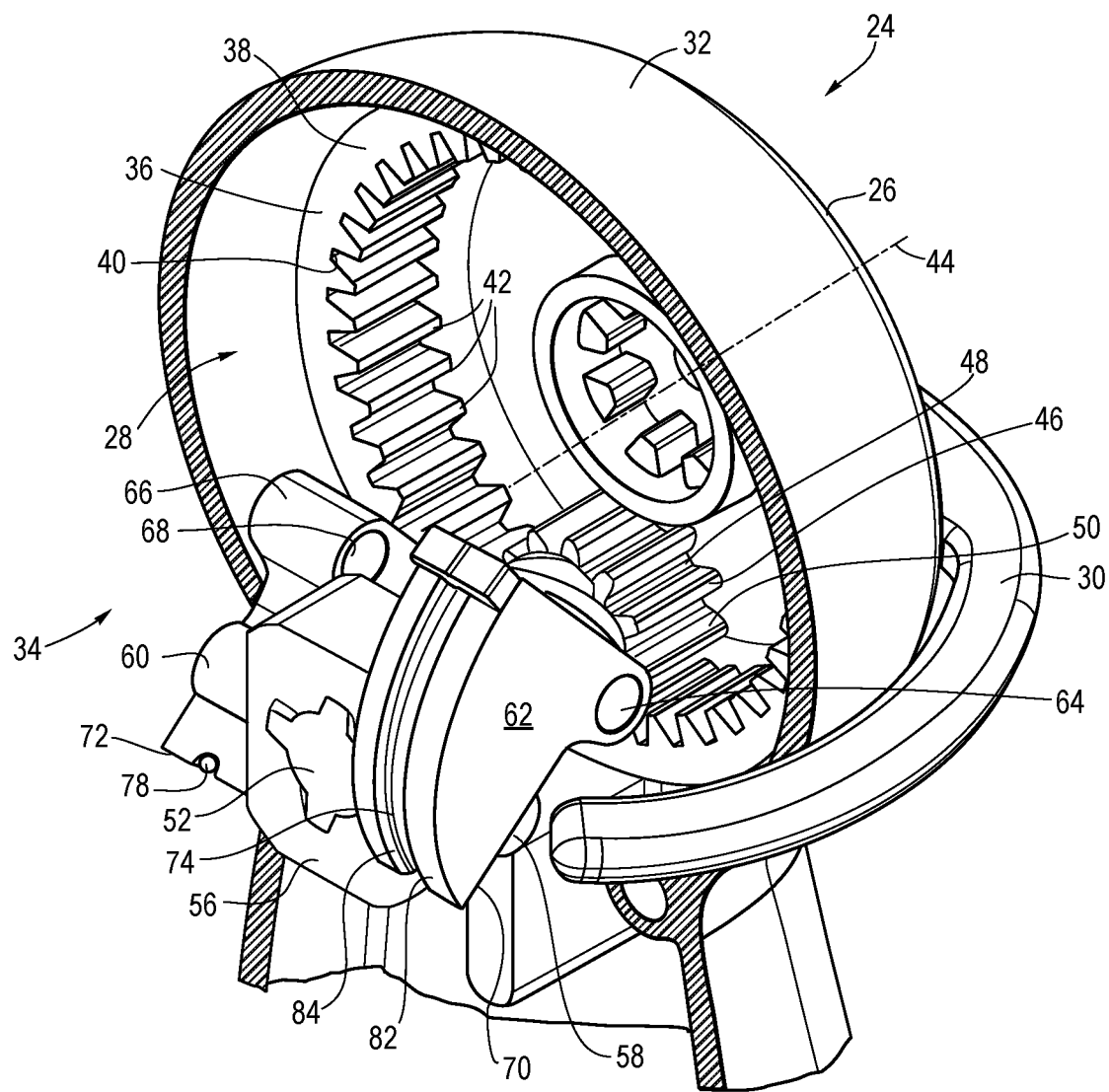
FIG. 6 is a sectional view of a portion of an example handle for an endoscope with a lever in a first position, according to various embodiments.

Referring now to FIGS. 1-6, in example embodiments an endoscope 10 or an endoscope system includes a catheter 12 having an elongate body 14 with a proximal end 16 and an opposing distal end 18. Elongate body 14 includes at least one passage, such as passage 20, that extends along a length of elongate body 14 between proximal end 16 and distal end 18. In example embodiments, a flexible distal tip portion 22 is coupled to elongate body 14 at distal end 18. A control, such as an example handle 24 shown in FIGS. 1-6, is coupled to proximal end 16 of elongate body 14. Handle 24 includes a housing 26 that defines an interior volume 28 of handle 24, as shown in FIGS. 5 and 6. In certain example embodiments, an additional catheter 29, power cord, or other suitable tubing, is coupled at a proximal end to handle 24. Additional catheter 29 has an elongate body including at least one passage extending along a length of the elongate body between the proximal end and the distal end of additional catheter 29.

Figure 1:
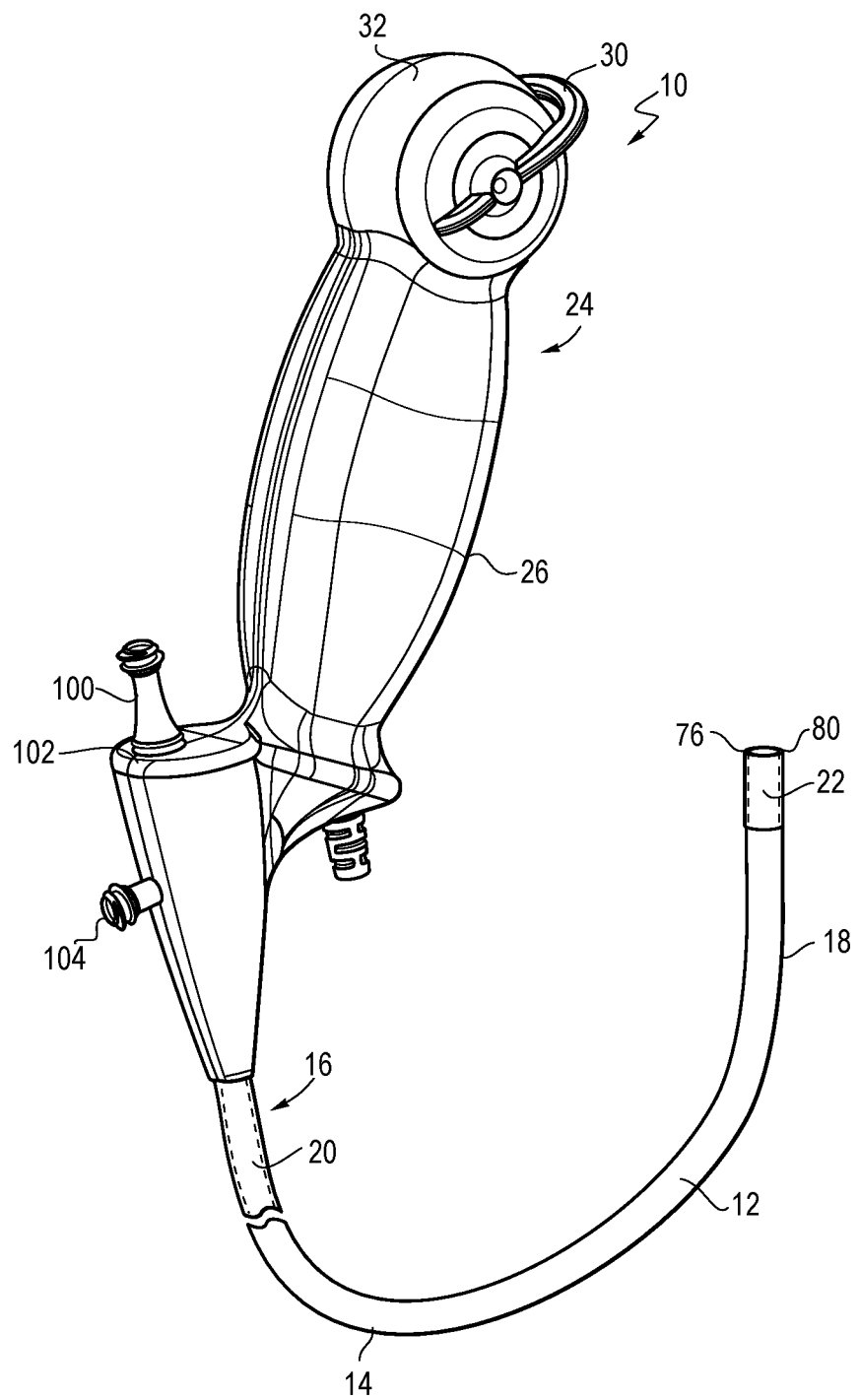
FIG. 1 is a perspective view of an example handle for an endoscope system, according to various embodiments.
Figure 2:
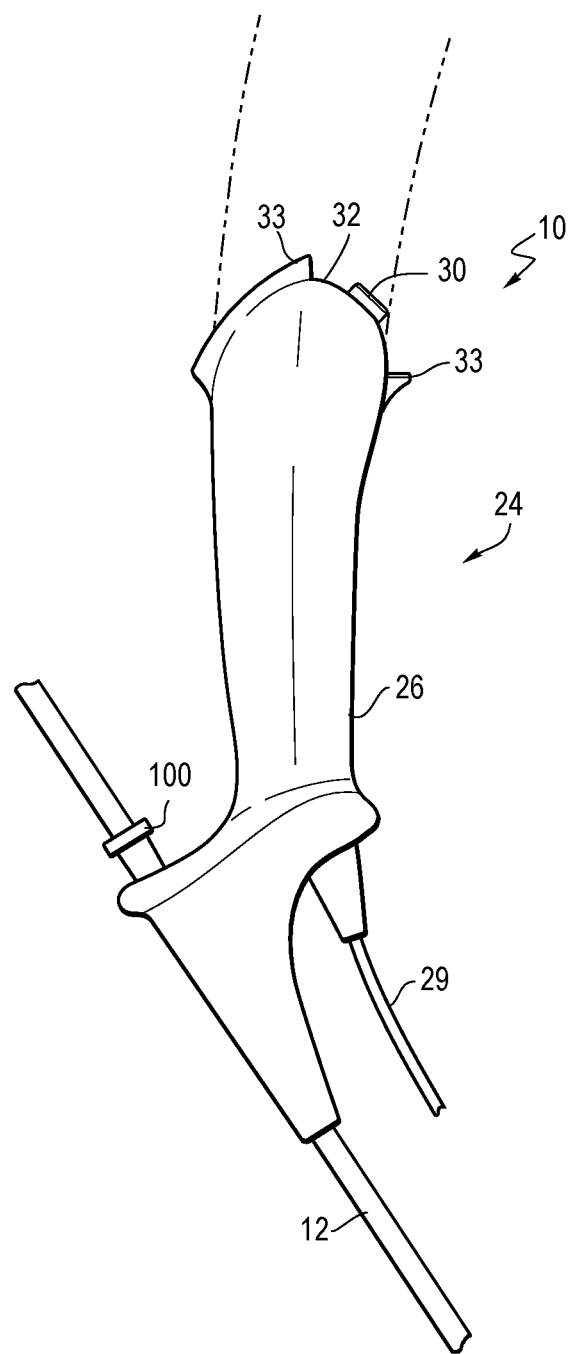
FIG. 2 is a plan view of an alternative example handle for an endoscope system, according to various embodiments.

As shown in FIGS. 1-6, a lever 30, such as a single-sided lever or a dual pivot lever, is external to housing 26. For example, in certain embodiments, lever 30 is positioned on an outer surface 32 of housing 26 and extends through a thickness of housing 26 into interior volume 28. In certain example embodiments, at least one stop 33 is formed on an outer surface of housing 24, as shown in FIG. 2. Stop 33 is configured to limit movement of lever 30 between the first position and the second position.

In example embodiments, a gear system 34 is positioned in interior volume 28. Gear system 34 is operatively coupled to lever 30. Referring further to FIGS. 5 and 6, gear system 34 includes a first gear 36 operatively coupled to lever 30. In example embodiments, first gear 36 is a ring gear 38, as shown in FIGS. 5 and 6, having a plurality of teeth on an inner annular surface 40. In alternative example embodiments, first gear 36 is a conventional gear having a plurality of teeth on an outer annular surface (not shown in FIGS. 1-6). First gear 36 has a plurality of first teeth 42 positioned about inner annular surface 40 of first gear 36. First gear 36 is rotatable about a first axis 44 as lever 30 is moved between a first position and a second position, e.g., from an initial or neutral position to a first position or from the initial position to a second position different from the first position.

A pinion 46 is operatively coupled to first gear 36, as shown in FIGS. 5 and 6. Pinion 46 has an outer surface 48 including a plurality of second teeth 50 configured to cooperate with, e.g., mesh with, the plurality of first teeth 42 such that pinion 46 rotates as first gear 36 rotates about first axis 44. In example embodiments, a gear ratio of the pinion to the first gear is between 2 to 1 and 6 to 1 and, more particularly, 4 to 1. A worm gear 52 is coaxially coupled to pinion 46. Worm gear 52 has at least one helical thread 54 extending along a length of worm gear 52.

A gear nut 56 is positioned about worm gear 52. In example embodiments, gear nut 56 defines an threaded passage (not shown in FIGS. 5 and 6) positioned about worm gear 52 that cooperates with helical thread 54 to move gear nut 56 along the length of worm gear 52 as worm gear 52 rotates with pinion 46. In example embodiments, a gear ratio of the gear nut to the worm gear is between 2 to 1 and 6 to 1 and, more particularly, 4 to 1. In example embodiment, gear nut 56 includes a first cam, such as a first post 58, and a second cam, such as second post 60, extending laterally outward from gear nut 56, as shown in FIGS. 5 and 6.

A first quadrant 62 is coupled to an inner surface of housing 26. As shown in FIGS. 5 and 6, first quadrant 62 contacts first post 58 such that as gear nut 56 moves in a first direction along a length of worm gear 52, first post 58 contacts first quadrant 62 to urge first quadrant 62 to pivot about a second axis 64. Similarly, a second quadrant 66 is coupled to an inner surface of housing 26. As shown in FIGS. 5 and 6, second quadrant 66 contacts second post 60 such that as gear nut 56 moves in a second direction opposite the first direction along a length of worm gear 52, second post 60 contacts second quadrant 66 to urge second quadrant 66 to pivot about a third axis 68 collinear with second axis 64.

In certain example embodiments, first quadrant 62 has a first surface 70 that contacts the first cam of gear nut 56 such that as gear nut 56 moves in a first direction along a length of worm gear 52, the first cam contacts first surface 70 to urge first quadrant 62 to pivot about second axis 64. Similarly, second quadrant 66 has a second surface 72 that contacts the second cam of gear nut 56 such that as gear nut 56 moves in a second direction opposite the first direction along a length of worm gear 52, the second cam contacts second surface 72 to urge second quadrant 66 to pivot about third axis 68. In example embodiments, movement of lever 30 in a first direction urges first quadrant 62 to pivot about second axis 64 and deflect flexible distal tip portion 22 in a corresponding first direction and movement of lever 30 in a second direction different from the first direction urges second quadrant 66 to pivot about third axis 68 and deflect flexible distal tip portion 22 in a corresponding second direction.

In certain example embodiments, a first wire 74 is coupled between first quadrant 62 and a first lateral side 76 of flexible distal tip portion 22. A second wire 78 is coupled between second quadrant 66 and a second lateral side 80 of flexible distal tip portion 22 opposite first lateral side 78. At least a portion of first quadrant 62 has an arcuate surface 82 forming a groove 84 configured to receive a proximal end of first wire 74 and at least a portion of second quadrant 66 has an arcuate surface 86 forming a groove 88 configured to receive a proximal end of second wire 78. In these example embodiments, movement of lever 30 in a first direction urges first quadrant 62 to pivot about second axis 64 to provide tension in first wire 74 and deflect flexible distal tip portion 22 in a corresponding first direction and movement of lever 30 in a second direction different from the first direction urges second quadrant 66 to pivot about third axis 68 to provide tension in second wire 78 and deflect flexible distal tip portion 22 in a corresponding second direction. In example embodiments, flexible distal tip portion 22 is configured to deflect in a plurality of directions.

In example embodiments, one or more biasing members (not shown), such as a suitable spring or another suitable biasing member, is operatively coupled to first quadrant 62 and/or second quadrant 66 and configured to bias first quadrant 62 and/or second quadrant 66 toward an initial or neutral position, as shown in FIG. 4. In example embodiments, at least a portion of first quadrant 62 has an arcuate surface 82 forming a groove 84 configured to receive a proximal end of first wire 74 and at least a portion of second quadrant 66 has an arcuate surface 86 forming a groove 88 configured to receive a proximal end of second wire 78.

Referring again to FIGS. 3 and 4, for example, in example embodiments, handle 24 is positioned about a primary longitudinal axis 90. An access channel 92 extends through housing 26 along a secondary axis 94. In the embodiments shown in FIGS. 3 and 4, secondary axis 94 intersects primary longitudinal axis 90 at an angle of 30° to 45°. In these embodiments, access channel 92 is in communication with passage 20 of elongate body 14. As shown for example in FIG. 4, in certain example embodiments, secondary axis 94 intersects primary longitudinal axis 90 at a point 96 offset with respect to an inlet 98 to passage 20 at proximal end 16 of elongate body 14. In certain example embodiments, the offset, i.e., a distance between the intersection of secondary axis 94 with primary longitudinal axis 90 and inlet 98, is about 0.5 inch to about 1.5 inch and, more particularly, 1.0 inch. As shown for example in FIG. 3, in certain example embodiments, secondary axis 94 intersects primary longitudinal axis 90 at inlet 98 to passage 20 at proximal end 16 of elongate body 14. As shown in FIGS. 1-4, a suitable fitting 100, such as a luer fitting, may be coupled to handle 24 at a proximal end 102 of access channel 92. As shown in FIG. 1, in example embodiments, a flush port 104 extends into housing 26 to provide communication with access channel 92.

In example embodiments, a control, e.g., a handle, for an endoscope is provided. The endoscope includes a catheter having a flexible distal tip portion. The control is coupled to a proximal end of a catheter and configured to control deflection of the flexible distal tip portion. The control includes a housing defining an interior volume. A lever external to the housing extends through the housing into the interior volume. A gear system is positioned in the interior volume and operatively coupled to the lever. The gear system includes a first gear coupled to the lever. The first gear has a plurality of first teeth positioned about an annular surface of the first gear. The first gear is rotatable about a first axis as the lever is moved from a first position to a second position. A pinion is operatively coupled to the first gear. The pinion has an outer surface that includes a plurality of second teeth configured to cooperate with the plurality of first teeth such that the pinion rotates as the first gear rotates about the first axis. A worm gear is coaxially coupled to the pinion. The worm gear has at least one helical thread extending along a length of the worm gear. A gear nut is positioned about the worm gear. The gear nut cooperates with the at least one helical thread to move along the length of the worm gear as the worm gear rotates with the pinion. The gear nut includes a first post and a second post extending laterally outward from the gear nut. A first quadrant contacts the first post such that as the gear nut moves in a first direction along a length of the worm gear, the first post contacts the first quadrant to urge the first quadrant to pivot about a second axis. A second quadrant contacts the second post such that as the gear nut moves in a second direction opposite the first direction along a length of the worm gear, the second post contacts the second quadrant to urge the second quadrant to pivot about a third axis collinear with the second axis, wherein movement of the lever in a first direction deflects the flexible distal tip portion in a corresponding first direction.

In example embodiments, a first wire is coupled between the first quadrant and a first lateral side of the flexible distal tip portion. A second wire is coupled between the second quadrant and a second lateral side of the flexible distal tip portion opposite the first lateral side. Movement of the lever in the first direction urges the first quadrant to pivot about the second axis to provide tension in the first wire and deflect the flexible distal tip portion in the corresponding first direction and movement of the lever in a second direction different from the first direction urges the second quadrant to pivot about the third axis to provide tension in the second wire and deflect the flexible distal tip portion in a corresponding second direction.

In example embodiments, a control, e.g., a handle, for an endoscope is provided. The endoscope includes a catheter having a flexible distal tip portion. The control is coupled to a proximal end of a catheter and configured to control deflection of the flexible distal tip portion. The control includes a housing defining an interior volume. A lever external to the housing extends through the housing into the interior volume. A gear system is positioned in the interior volume and operatively coupled to the lever. The gear system includes a worm gear operatively coupled to the lever. The worm gear has at least one helical thread extending along a length of the worm gear. A gear nut is positioned about the worm gear. The gear nut cooperates with the at least one helical thread to move along the length of the worm gear as the worm gear rotates with the pinion. The gear nut includes a first cam and a second cam. A first quadrant has a first surface that contacts the first cam such that as the gear nut moves in a first direction along a length of the worm gear, the first cam contacts the first surface to urge the first quadrant to pivot about a first axis. A second quadrant has a second surface that contacts the second cam such that as the gear nut moves in a second direction opposite the first direction along a length of the worm gear, the second cam contacts the second surface to urge the second quadrant to pivot about a second axis collinear with the first axis. In these embodiments, movement of the lever in a first direction urges the first quadrant to pivot about the first axis and deflect the flexible distal tip portion in a corresponding first direction and movement of the lever in a second direction different from the first direction urges the second quadrant to pivot about the second axis and deflect the flexible distal tip portion in a corresponding second direction.

In example embodiments, a first wire is coupled between the first quadrant and a first lateral side of the flexible distal tip portion. A second wire is coupled between the second quadrant and a second lateral side of the flexible distal tip portion opposite the first lateral side. In these embodiments, rotation of the first quadrant about the first axis provides tension in the first wire to deflect the flexible distal tip portion in the corresponding first direction and rotation of the second quadrant about the second axis provides tension in the second wire to deflect the flexible distal tip portion in the corresponding second direction.

Endoscopes evolved from line-of-sight tubes wherein the optics demanded a straight pathway to convey the image. More recent conventional technology is able to convey images via non-linear pathways. As a result, in example embodiments, the working channel or catheter passage is straight to enhance torqueability while reducing friction and wear. Among other aspects, the off-angle nature of the "nose" of the handle differentiates it from conventional handles, while facilitating a better clinical outcome. The single-use nature of the handle saves time and money while preventing or limiting cross-contamination. The handle is aesthetically pleasing and provides excellent functionality, while reducing the cost of manufacturing due to more efficient internal mechanisms. With a decrease in internal components and no over-molded features, the device generates less waste and costs less to warehouse and ship. Moreover, the relatively light weight and reduced friction put less stress on the operator.

In certain example embodiments, the housing and its internal components may be injection molded from a single type of plastic to ease sourcing and recycling. The device is designed for over-hand use by left-handed or right-handed operators. The device may be sterilized using ethylene oxide or hydrogen peroxide. The "steering" lever actuates and/or rotates a worm gear that drives the wires or steering cable pulleys so that there is no need for a steering brake. There is a straight path from the luer fitting to the catheter in the access channel so that tools placed therethrough do not have to negotiate a tortuous path in either direction.

FIGS. 1-6 show a general shape, proportions and size of the handle. In example embodiments, a power and/or data cord enters and/or exits the handle at an end as the catheter. FIG. 2 shows a more tapered and curved version. FIG. 3 shows a more bulbous handle which may be necessary to maintain a good grip under wet conditions. It has a tip angle of 30 degrees from the primary longitudinal axis. FIG. 4 shows a bulbous handle with a 45-degree tip angle. FIGS. 5 and 6 show the inventive tip-deflecting mechanism inside the handle. In example embodiments, the ring gear has approximately four times (4×) as many teeth as the pinion or spur gear with which it meshes. The worm gear is on the same shaft as the pinion or spur gear. The worm gear is a fast-travel lead-screw which has four threads (4 starts) in certain embodiments, that may or may not be ACME threads. The gear nut has cams or posts on both sides which bear against the surfaces of each quadrant. Each quadrant includes a fitting to hold a proximal end of the wire or cable, and a surface which bears against a respective cam or post of the gear nut. FIG. 5 shows the lever and associated components in the neutral position. FIG. 6 shows the lever and associated components in a first of two opposing deflected-positions, in certain example embodiments.

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

One skilled in the art will realize that a virtually unlimited number of variations to the above descriptions are possible, and that the examples and the accompanying figures are merely to illustrate one or more examples of implementations.

It will be understood by those skilled in the art that various other modifications can be made, and equivalents can be substituted, without departing from claimed subject matter. Additionally, many modifications can be made to adapt a particular situation to the teachings of claimed subject matter without departing from the central concept described herein. Therefore, it is intended that claimed subject matter not be limited to the particular embodiments disclosed, but that such claimed subject matter can also include all embodiments falling within the scope of the appended claims, and equivalents thereof.

In the detailed description above, numerous specific details are set forth to provide a thorough understanding of claimed subject matter. However, it will be understood by those skilled in the art that claimed subject matter can be practiced without these specific details. In other instances, methods, devices, or systems that would be known by one of ordinary skill have not been described in detail so as not to obscure claimed subject matter.

Reference throughout this specification to "one embodiment" or "an embodiment" can mean that a particular feature, structure, or characteristic described in connection with a particular embodiment can be included in at least one embodiment of claimed subject matter. Thus, appearances of the phrase "in one embodiment" or "an embodiment" in various places throughout this specification are not necessarily intended to refer to the same embodiment or to any one particular embodiment described. Furthermore, it is to be understood that particular features, structures, or characteristics described can be combined in various ways in one or more embodiments as will be appreciated by those of skill in the art. In general, of course, these and other issues can vary with the particular context of usage. Therefore, the particular context of the description or the usage of these terms can provide helpful guidance regarding inferences to be drawn for that context.

We claim:

1. An endoscope, comprising:
a catheter having an elongate body with a proximal end and an opposing distal end, the elongate body including a passage extending along a length of the elongate body between the proximal end and the distal end and a flexible distal tip portion coupled to the elongate body;
a handle coupled to the proximal end of the elongate body, the handle comprising:
a housing defining an interior volume;
a lever on an outer surface of the housing and extending through a thickness of the housing into the interior volume;
a gear system positioned in the interior volume and operatively coupled to the lever, the gear system including:
a first gear coupled to the lever, the first gear having a plurality of first teeth positioned about an annular surface of the first gear, the first gear rotatable about a first axis as the lever is moved between a first position and a second position;
a pinion operatively coupled to the first gear, the pinion having an outer surface including a plurality of second teeth configured to cooperate with the plurality of first teeth such that the pinion rotates as the first gear rotates about the first axis;
a worm gear coaxially coupled to the pinion, the worm gear having at least one helical thread extending along a length of the worm gear;
a gear nut positioned about the worm gear, the gear nut cooperating with the at least one helical thread to move along the length of the worm gear as the worm gear rotates, the gear nut including a first post and a second post extending laterally outward from the gear nut;
a first quadrant contacting the first post such that as the gear nut moves in a first direction along a length of the worm gear the first post contacts the first quadrant to urge the first quadrant to pivot about a second axis; and
a second quadrant contacting the second post such that as the gear nut moves in a second direction opposite the first direction along a length of the worm gear the second post contacts the second quadrant to urge the second quadrant to pivot about a third axis collinear with the second axis;
a first wire coupled between the first quadrant and a first lateral side of the flexible distal tip portion; and
a second wire coupled between the second quadrant and a second lateral side of the flexible distal tip portion opposite the first lateral side,
wherein movement of the lever in a first direction urges the first quadrant to pivot about the second axis to provide tension in the first wire and deflect the flexible distal tip portion in a corresponding first direction and movement of the lever in a second direction different from the first direction urges the second quadrant to pivot about the third axis to provide tension in the second wire and deflect the flexible distal tip portion in a corresponding second direction.

2. The endoscope of claim 1, wherein the plurality of first teeth is positioned about one of an outer annular surface of the first gear and an inner annular surface of the first gear.

3. The endoscope of claim 1, wherein the flexible distal tip portion is configured to deflect in a plurality of directions.

4. The endoscope of claim 1, further comprising a biasing member operatively coupled to the first quadrant and configured to bias the first quadrant toward a neutral position.

5. The endoscope of claim 1, wherein at least a portion of the first quadrant has an arcuate outer surface forming a groove configured to receive a proximal end of the first wire.

6. The endoscope of claim 1, wherein a gear ratio of the pinion to the first gear is between 2 to 1 and 6 to 1.

7. The endoscope of claim 1, wherein a gear ratio of the gear nut to the worm gear is between 2 to 1 and 6 to 1.

8. The endoscope of claim 1, wherein the handle is positioned about a primary longitudinal axis, the endoscope further comprising an access channel extending through the housing along a secondary axis, the secondary axis intersecting the primary longitudinal axis at an angle of 30° to 45°, the access channel in communication with the passage of the elongate body.

9. The endoscope of claim 8, wherein the secondary axis intersects the primary longitudinal axis at a point offset with respect to an inlet to the passage at the proximal end of the elongate body.

10. The endoscope of claim 8, wherein the secondary axis intersects the primary longitudinal axis at an inlet to the passage at the proximal end of the elongate body.

11. The endoscope of claim 8, further comprising a fitting coupled to the handle at a proximal end of the access channel.

12. The endoscope of claim 8, further comprising a flush port extending into the housing and in communication with the access channel.

13. The endoscope of claim 1, further comprising at least one stop on the outer surface of the housing, the at least one stop configured to limit movement of the lever between the first position and the second position.

14. The endoscope of claim 1, further comprising an additional catheter coupled at a proximal end to the handle, the additional catheter having an elongate body including a passage extending along a length of the elongate body between the proximal end and the distal end.

15. A control for an endoscope including a catheter having a flexible distal tip portion, the control coupled to a proximal end of the catheter and configured to control deflection of the flexible distal tip portion, the control comprising:
a housing defining an interior volume;
a lever external to the housing and extending through the housing into the interior volume;
a gear system positioned in the interior volume and operatively coupled to the lever, the gear system including:
a first gear coupled to the lever, the first gear having a plurality of first teeth positioned about an annular surface of the first gear, the first gear rotatable about a first axis as the lever is moved between a first position and a second position;
a pinion operatively coupled to the first gear, the pinion having an outer surface including a plurality of second teeth configured to cooperate with the plurality of first teeth such that the pinion rotates as the first gear rotates about the first axis;
a worm gear coaxially coupled to the pinion, the worm gear having at least one helical thread extending along a length of the worm gear;
a gear nut positioned about the worm gear, the gear nut cooperating with the at least one helical thread to move along the length of the worm gear as the worm gear rotates, the gear nut including a first post and a second post extending laterally outward from the gear nut;

a first quadrant contacting the first post such that as the gear nut moves in a first direction along a length of the worm gear the first post contacts the first quadrant to urge the first quadrant to pivot about a second axis; and a second quadrant contacting the second post such that as the gear nut moves in a second direction opposite the first direction along a length of the worm gear the second post contacts the second quadrant to urge the second quadrant to pivot about a third axis collinear with the second axis, wherein movement of the lever in a first direction toward the first position deflects the flexible distal tip portion in a corresponding first direction.

16. The control of claim 15, further comprising:

a first wire coupled between the first quadrant and a first lateral side of the flexible distal tip portion; and a second wire coupled between the second quadrant and a second lateral side of the flexible distal tip portion opposite the first lateral side, wherein movement of the lever in the first direction urges the first quadrant to pivot about the second axis to provide tension in the first wire and deflect the flexible distal tip portion in the corresponding first direction and movement of the lever in a second direction different from the first direction urges the second quadrant to pivot about the third axis to provide tension in the second wire and deflect the flexible distal tip portion in a corresponding second direction.

17. A control for an endoscope including a catheter having a flexible distal tip portion, the control coupled to a proximal end of a catheter and configured to control deflection of the flexible distal tip portion, the control comprising:

a housing defining an interior volume;

a lever external to the housing and extending through the housing into the interior volume;

a gear system positioned in the interior volume and operatively coupled to the lever, the gear system including:

a worm gear operatively coupled to the lever, the worm gear having at least one helical thread extending along a length of the worm gear;

a gear nut positioned about the worm gear, the gear nut cooperating with the at least one helical thread to move along the length of the worm gear as the worm gear rotates, the gear nut including a first cam and a second cam;

a first quadrant having a first surface contacting the first cam such that as the gear nut moves in a first direction along a length of the worm gear the first cam contacts the first surface to urge the first quadrant to pivot about a first axis; and a second quadrant having a second surface contacting the second cam such that as the gear nut moves in a second direction opposite the first direction along a length of the worm gear the second cam contacts the second surface to urge the second quadrant to pivot about a second axis collinear with the first axis, wherein movement of the lever in a first direction urges the first quadrant to pivot about the first axis and deflect the flexible distal tip portion in a corresponding first direction and movement of the lever in a second direction different from the first direction urges the second quadrant to pivot about the second axis and deflect the flexible distal tip portion in a corresponding second direction.

18. The control of claim 17, further comprising:

a first wire coupled between the first quadrant and a first lateral side of the flexible distal tip portion; and a second wire coupled between the second quadrant and a second lateral side of the flexible distal tip portion opposite the first lateral side, wherein rotation of the first quadrant about the first axis provides tension in the first wire to deflect the flexible distal tip portion in the corresponding first direction and rotation of the second quadrant about the second axis provides tension in the second wire to deflect the flexible distal tip portion in the corresponding second direction.

* * * * *